United States Patent [19]

Markezich

[11] 4,011,246

[45] Mar. 8, 1977

[54] 2-[4-(3,4-DICARBOXYPHENOXY)PHENYL]-2-(4-HYDROXYPHENYL)PROPANE AND THE ANHYDRIDES THEREOF

[75] Inventor: Ronald L. Markezich, Scotia, N.Y.

[73] Assignee: General Electric Company, Schenectady, N.Y.

[22] Filed: Apr. 14, 1976

[21] Appl. No.: 676,855

[52] U.S. Cl. .................. 260/346.3; 260/520 E
[51] Int. Cl.$^2$ .................................. C07D 307/89
[58] Field of Search .................. 260/346.3, 520

[56] References Cited

UNITED STATES PATENTS 3,972,902   8/1976   Heath et al. .................. 260/346.3

Primary Examiner—Henry R. Jiles
Assistant Examiner—Bernard Dentz
Attorney, Agent, or Firm—Joseph T. Cohen; Jerome C. Squillaro

[57] ABSTRACT

This invention covers a novel bisphenol-A diacid and a bisphenol-A anhydride.

3 Claims, No Drawings

2-[4-(3,4-DICARBOXYPHENOXY)PHENYL]-2-(4-HYDROXYPHENYL)PROPANE AND THE ANHYDRIDES THEREOF

This invention is concerned with a novel bisphenol-A acid and a novel bisphenol-A anhydride. More particularly, the invention is concerned with two bisphenol-A compounds selected from the class consisting of 2-[4-(3,4-dicarboxyphenoxy)-phenyl]-2-(4-hydroxyphenyl)propane having the formula

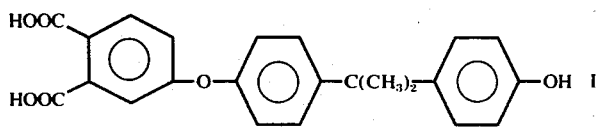

and a bisphenol-A anhydride prepared from I, 2-[4-(3,4-dicarboxyphenoxy)-phenyl]-2-(4-hydroxyphenyl)propane anhydride having the formula

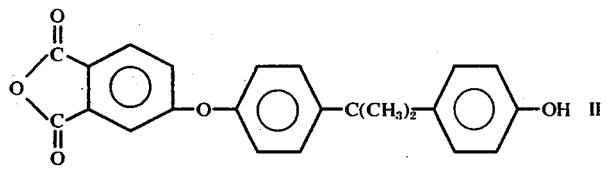

The above compounds are both derived from a mono-imide of the formula

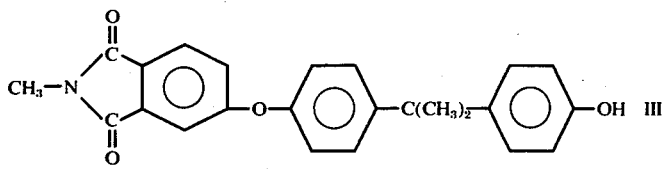

which is prepared by effecting reaction between bisphenol-A and 4-nitro-N-methylphthalimide in the presence of either an alkali-metal hydroxide or an alkali-metal fluoride other than sodium fluoride. There is thus obtained a mixture of ingredients in which the mono-imide of formula III is present, which is then separated and by a series of hydrolysis steps and dehydration steps, one obtains successively the dicarboxylic acid derivative of formula I and the mono-anhydride derivative of formula II.

In order that those skilled in the art may better understand how the present invention may be practiced, the following examples are given by way of illustration and not be way of limitation. All reactions were conducted using a reflux condenser under a nitrogen atmosphere with stirring.

EXAMPLE 1

A mixture of 5.529 grams (26.8 mmole) of 4-nitro-N-methylphthalimide, 2.735 grams (12.8 mmole) BPA, 1.596 grams (27.5 mmole) anhydrous KF, and 50 ml anhydrous DMF was heated under a nitrogen atmosphere for 16 hours at the reflux temperature of the mass (about 153° C.). After cooling to room temperature (about 25° C.), the mixture was filtered to remove inorganic salts, and the filtrate was poured into 250 ml 0.2N aqueous HCl solution to remove DMF. Extraction with $CH_2Cl_2$ (two 150 ml portions), drying of the organic layer over anhydrous sodium sulfate and concentration in vacuum gave a reaction product which contained 58% of the bisphenol-A bisimide (BPA-BI) of the formula

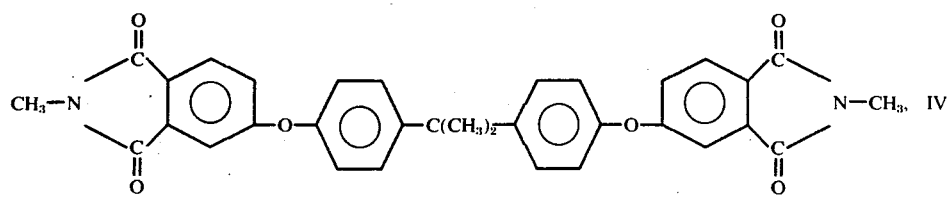

and 5% of the bisether

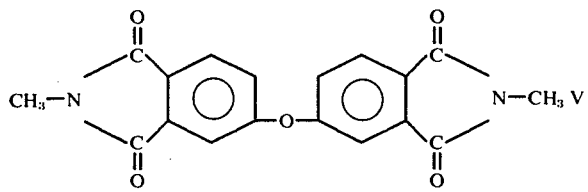

and 28% of the mono-imide of formula III. The above-identified process for obtaining the imides of formulas IV and V are more particularly disclosed and claimed in my copending application Ser. No. 676,993 filed concurrently with the instant application, and assigned to the same assignee as the present invention, and by reference is made part of the disclosures of the instant application. The aforesaid reaction product was separated into its components by chromatography on a silica gel column by elution with 6%/94% (by volume) ethyl acetate/CH$_2$Cl$_2$ to yield two fractions Fraction I — BPA-BI of formula IV Fraction II — mono-imide of formula II.

Fraction II was further purified by preparative thin-layer chromatography on silica gel (eluting with 10%/90% by volume ethyl acetate/CH$_2$Cl$_2$) to give 0.963 gram of a solid material having a melting point of 133°–136° C. and identified by proton, $^{13}$C nmr and by its mass spectrum as having formula III.

EXAMPLE 2

Into a reaction vessel fitted with heating means, magnetic stirrer, reflux condenser and nitrogen inlet, was placed 0.319 gram (0.82 mmole) of the mono-imide of formula III obtained in Example 1, and 6 ml of 1.0N aqueous potassium hydroxide. This mixture was stirred and heated at the reflux temperature (about 100° C.) of the mass for about 60 hours. After cooling to room temperature, the solution thus obtained was acidified with 12N hydrochloric acid to a pH of 1. Extraction with diethyl ether (two 25 ml portions) and two 25 ml portions methylene chloride, combining the organic fractions and drying over anhydrous sodium sulfate and finally concentrating the mixture in vacuum yielded 0.303 gram (94% yield) of the dicarboxy derivative of formula I having a melting point of 96°–100° C. when determined in an evacuated capillary. The structure of this compound was clearly established by proton nmr spectrum (dimethyl sulfoxide-d$_6$).

EXAMPLE 3

Into a reaction flask was placed 0.093 gram (0.02 mmole) of the dicarboxy compound of formula I described in Example 2. The reaction vessel was attached to a vacuum line (evacuated to 0.5 mm.) and heated to 180° C. over a 15 minute period. It was held at this temperature for 5 minutes and then cooled to room temperature to yield 0.81 gram (91% yield) of the bisphenol-A mono-anhydride of formula II having a melting point of 70°–75° C. when determined in an evacuated capillary tube. The structure of this compound was established conclusively by proton nmr spectrum as in Example 2. The molecular weight of this compound was also determined by peak matching on a mass spectrometer and showed for the formula C$_{23}$H$_{18}$O$_5$ a molecular weight of 374.1144 as contrasted with a theoretical value of 374.1154.

The aforesaid dicarboxylic acid anhydrides of formulas I and II respectively have many uses. Generally they have uses as curing agents for epoxy resins and as intermediates in the preparation of other compositions. For instance, the aforesaid dicarboxylic acid compound of formula I can be dehydrated as is done in Example 3 to give the compound having the structure identified by formula II. The mono-anhydride of formula II can be reacted with a hydroxyorganic amine of the general formula

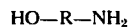

where R is a divalent hydrocarbon radical, for instance alkyl radicals of from 1 to 5 carbon atoms, arylene radicals, etc. to give compounds of the general formula

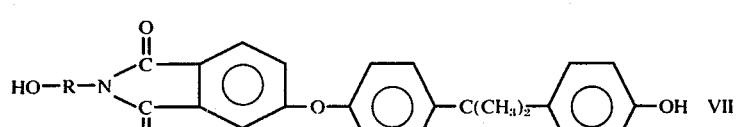

Treatment of this latter dihydroxy compound with phosgene gives polycarbonate resins of the formula

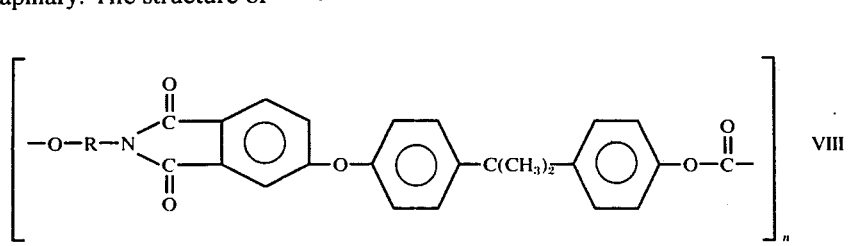

where R has the meaning given above and $n$ is a whole number greater than 1, e.g., 10 to 1000 or more.

The reaction of the compound of formula VII with isocyanates having the general formula

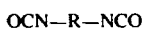    IX will yield polymeric structures of the general formula

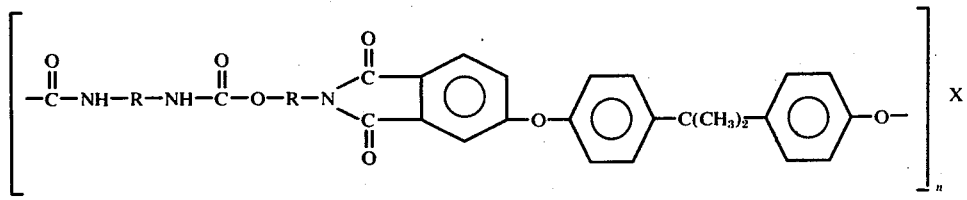

where R and n have the meanings given above.

Alternatively, the anhydride of formula II can be reacted with organic diamines of the general formula

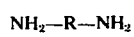    XI in a molar ratio of 2 mols of the compound of formula II per mol of the compound of formula XI to give a dihydroxy compound of the formula

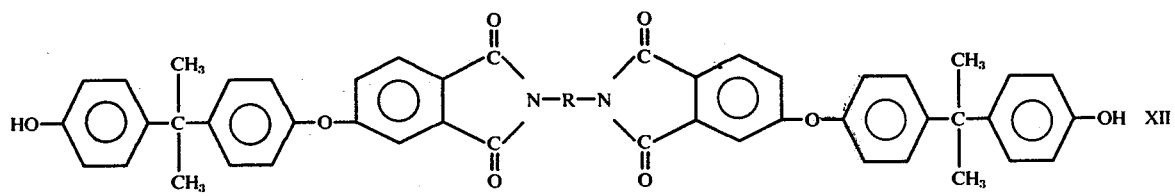

Treatment of the latter dihydroxy compound with phosgene will give polycarbonate resins of the formula

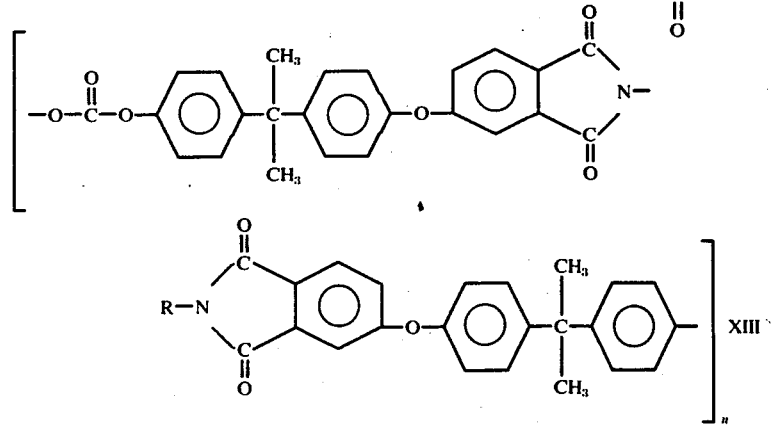

where R and n have the meanings given above.

The above-described polymeric compositions, whether filled or unfilled, can be employed in applications requiring good mechanical, electrical, and heat resistance properties. They are eminently suitable for use in the manufacture of glazing products, insulators, transformer blocks, motor armatures, printed circuits, honeycomb structure panels, compressor vanes, etc. In the form of solutions with suitable solvents, they can be used to coat electrical conductors such as copper or aluminum wire and the material so deposited can be heat-treated to effect conversion to the finally polymerized state.

I claim:

1. A bisphenol-A compound selected from the class consisting of a compound having the formula

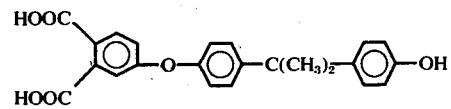

and a compound having the formula

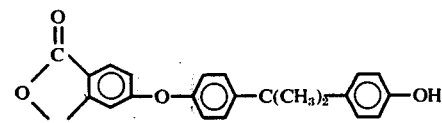

2. The compound having the formula
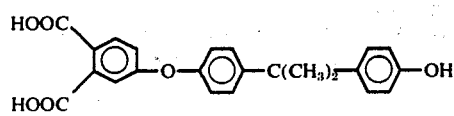
3. The compound having the formula
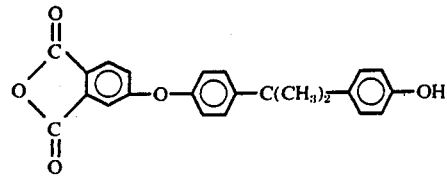
* * * * *